US007169109B2

(12) United States Patent
Jansen et al.

(10) Patent No.: US 7,169,109 B2
(45) Date of Patent: Jan. 30, 2007

(54) METHODS AND APPARATUS FOR CONTROLLING HEART ASSIST DEVICES

(75) Inventors: Jozef Reinier Cornelis Jansen, Noordwijkerhout (NL); Johannes Jacobus Schreuder, Varese (IT)

(73) Assignee: Arrow International, Inc., Reading, PA (US)

( * ) Notice: Subject to any disclaimer, the term of this patent is extended or adjusted under 35 U.S.C. 154(b) by 523 days.

(21) Appl. No.: 10/297,118

(22) PCT Filed: Oct. 1, 2001

(86) PCT No.: PCT/NL01/00713

§ 371 (c)(1),
(2), (4) Date: Sep. 11, 2003

(87) PCT Pub. No.: WO02/28280

PCT Pub. Date: Apr. 11, 2002

(65) Prior Publication Data

US 2004/0059183 A1    Mar. 25, 2004

(30) Foreign Application Priority Data

Oct. 3, 2000 (NL) .................................. 1016320

(51) Int. Cl.
*A61B 5/02* (2006.01)
*A61M 1/10* (2006.01)
*A61N 1/362* (2006.01)

(52) U.S. Cl. .......................... 600/481; 600/16; 600/17; 600/18; 623/3.28; 623/3.1

(58) Field of Classification Search ............ 600/16–18, 600/481; 623/3.28, 3.1
See application file for complete search history.

(56) References Cited

U.S. PATENT DOCUMENTS 3,965,339 A    6/1976    Mount et al.

(Continued)

FOREIGN PATENT DOCUMENTS

EP    0 402 872 A1    12/1990

(Continued)

OTHER PUBLICATIONS

Eidenvall, Lars, et al., entitled "Information in the Aortic Blood Velocity Signal—A Simulation Study," Annual International Conference of the IEEE Engineering in Medicine and Biology Society, vol. 13, No. 5, 1991, pp. 2248-2249.

(Continued)

*Primary Examiner*—Robert E. Pezzuto
*Assistant Examiner*—Natasha Patel
(74) *Attorney, Agent, or Firm*—Amster, Rothstein & Ebenstein LLP

(57) ABSTRACT

An apparatus for a heart assist device, comprising a processing unit for computing the blood flow rate from the arterial pressure curve and for predicting at every heartbeat the closing time of the heart valve from the curve of the blood flow rate. The processing unit is adapted to deliver a signal for controlling a heart assist device at a point in time, a period ahead in time of the closing time of the heart valve, wherein the mechanical properties of the said heart assist device are taken into account in determining the period. The apparatus adapts itself to changes in a patient's heart frequency and aortic pressure.

14 Claims, 3 Drawing Sheets

U.S. PATENT DOCUMENTS

| | | | |
|---|---|---|---|
| 4,692,148 A | 9/1987 | Kantrowitz et al. | |
| 4,697,574 A | 10/1987 | Karcher et al. | |
| 4,794,910 A * | 1/1989 | Mushika | 600/18 |
| 4,809,681 A | 3/1989 | Kantrowitz et al. | |
| 5,169,379 A | 12/1992 | Freed et al. | |
| 5,178,151 A * | 1/1993 | Sackner | 600/485 |
| 5,265,011 A | 11/1993 | O'Rouke | |
| 5,365,933 A | 11/1994 | Elghazzawi | |
| 5,390,679 A | 2/1995 | Martin | |
| 5,713,954 A | 2/1998 | Rosenberg | |
| 5,882,311 A | 3/1999 | Orouke | |
| 6,010,457 A | 1/2000 | O'Rouke | |
| 6,258,035 B1 * | 7/2001 | Hoeksel et al. | 600/481 |
| 6,569,103 B2 | 5/2003 | Hoeksel et al. | |
| 6,679,829 B2 * | 1/2004 | Nigroni et al. | 600/18 |

FOREIGN PATENT DOCUMENTS

| | | |
|---|---|---|
| JP | 63-242267 | 10/1988 |
| JP | 01-297073 A | 11/1989 |
| WO | WO 92/12669 | 8/1992 |
| WO | WO 97/24690 | 7/1997 |

OTHER PUBLICATIONS

Luisada, A.A. et al. On the function of the aortic valve and the mechanism of the first and second sounds. Japanese Heart Journal, vol. 18(1), Jan. 1977, pp. 81-91.

Portaluppi, F., et al., entitiled "Transmission Delays of Different Portions of the Aterial Pulse—A Comparison Between the Indirect Aortic and Carotid Pulse Tracings," Acta Cardiologica, vol. 38, No. 1, 1983, pp. 49-59.

* cited by examiner

METHODS AND APPARATUS FOR CONTROLLING HEART ASSIST DEVICES

CROSS-REFERENCE TO RELATED APPLICATIONS

This application is a 35 U.S.C. §371 national stage filing of PCT International Application No. PCT/NL01/00713, filed Oct. 1, 2001, which claims priority of Dutch Patent Application No. 1016320, filed Oct. 3, 2000, the contents of both of which are hereby incorporated by reference.

FIELD OF THE INVENTION

The invention relates to methods and apparatus for controlling a heart assist device, for example intra-aortic balloon pumps and auxiliary artificial hearts.

BACKGROUND OF THE INVENTION

An intra-aortic balloon pump (IABP) comprises an intra-aortic balloon (IAB) and a pump device, wherein the IAB can be introduced for example into the aorta of a patient whose heart does not function properly.

With every cardiac cycle, the IAB is inflated by means of a pump device at the end of an ejection phase of the left ventricle of the heart and deflated again before the next ejection phase begins. In this way, the pump action of the heart is improved and there is an improvement of the blood supply to the coronary artery. For a correct operation it is of importance that the IAB be inflated and deflated at the correct times in the cardiac cycle. In particular the correct timing in the cardiac cycle of the inflation of the balloon is very important, because premature inflation of the IAB, before the end of the ejection phase of the heart, can cause the ejection phase of the heart to stop, as a result of which the blood flow rate is reduced. In the case of too late inflation of the IAB, its operation will be less effective. The blood volume that is pumped by the IAB to the coronary arteries and to the vascular system will be smaller in that case, and the reduction of the after load on the heart during the ejection phase will be smaller.

The times of inflation and deflation of the IAB can be set manually at fixed times within the cardiac cycle by a skilled person, for example on basis of the electrocardiogram (ECG) of the heart. A disadvantage of this system is that the times that have been set will deviate from the desired times with every acceleration or deceleration of the cardiac cycle, so that said times constantly need to be reset. Furthermore it is impossible to take into account the possibility of an irregular cardiac cycle, which often occurs with those people for whom the IABP is intended. Thereby, in particular the setting of the inflation time of the IAB is carried out incorrectly in many cases.

U.S. Pat. No. 4,809,681 discloses an apparatus for controlling an IABP which determines the time at which the IAB is to be deflated on the basis of the ECG. However, the time at which the IAB is to be inflated cannot be determined by means of said apparatus.

From Sakamoto et al, ASAIO Journal 1995, pp. 79–83, there is known an apparatus which predicts the position of the incisura point in the cardiac cycle—i.e. the closing time of the heart valve—on the basis of the ECG and by computing the duration of the ejection phase from the period of time of the preceding heartbeat. Said apparatus is not accurate enough in those cases where the heartbeat is irregular.

U.S. Pat. No. 5,183,051 discloses a device by means of which it is attempted to determine the incisura point by looking for a dip in the arterial pressure signal within a predetermined time interval within the cardiac cycle. Said device is not accurate enough in the case of a damped blood pressure signal or in the case of irregular heartbeats. Furthermore, no mention is made in said document of an apparatus for controlling an IABP.

WO 9724690 discloses an apparatus which determines the closing time of the aortic valve by means of a Windkessel model. Said apparatus also functions in those cases where the heartbeat is irregular. However, even a correct determination of the closing time of the aortic valve (incisura point) results in a too late inflation of the intra-aortic balloon due to the mechanical properties of an IABP system.

The object of the invention is to provide an apparatus of the above-mentioned type which does not exhibit the above drawbacks.

SUMMARY OF THE INVENTION

To this end the invention provides an apparatus for controlling a heart assist device, comprising a processing unit for computing the blood flow rate from the arterial pressure curve and for predicting at every heartbeat the closing time of the heart valve from the curve of the blood flow rate, wherein the processing unit is adapted to deliver a signal for controlling a heart assist device at a point in time, a period ahead in time of the closing time of the heart valve, wherein the mechanical properties of said heart assist device are taken into account in determining said period.

In this manner an apparatus is obtained, wherein the mechanical properties of such a heart assist device are taken into account and wherein the apparatus adapts itself to changes in the heart frequency and the aortic blood pressure.

A suitable embodiment is a real time computing programme based on a Windkessel model which comprises three elements, namely a characteristic input resistance, Rao, an arterial compliance, Cw, and a peripheral resistance, Rp. Rao is the resistance that is experienced by the heart, Cw is the compliance which represents the ability of the arterial vascular bed to store a specific volume of blood by means of elastic expansion, and Rp is the peripheral resistance beyond which the stored volume of blood runs off. An advantage of the three-element Windkessel model is that the shape of the computed blood flow rate depends to a minor degree on the values that are used for the elements. As a result, the closing time of the aortic valve can be predicted with great accuracy and thereby the heart assist device can be controlled in an effective manner.

The values that are used for the elements in the Windkessel model are known from literature, for example Am. J. Physiol. 1988, 255 (Heart Circ. Physiol.) H742–H753.

Better results are achieved if the dependence of the momentaneous blood pressure on the elasticity in the aorta is taken into account, as disclosed in WO 9212669.

The invention will now be explained in more detail with reference to the drawing, which schematically shows an embodiment of the apparatus according to the invention.

DETAILED DESCRIPTION OF THE INVENTION

Figure 1:
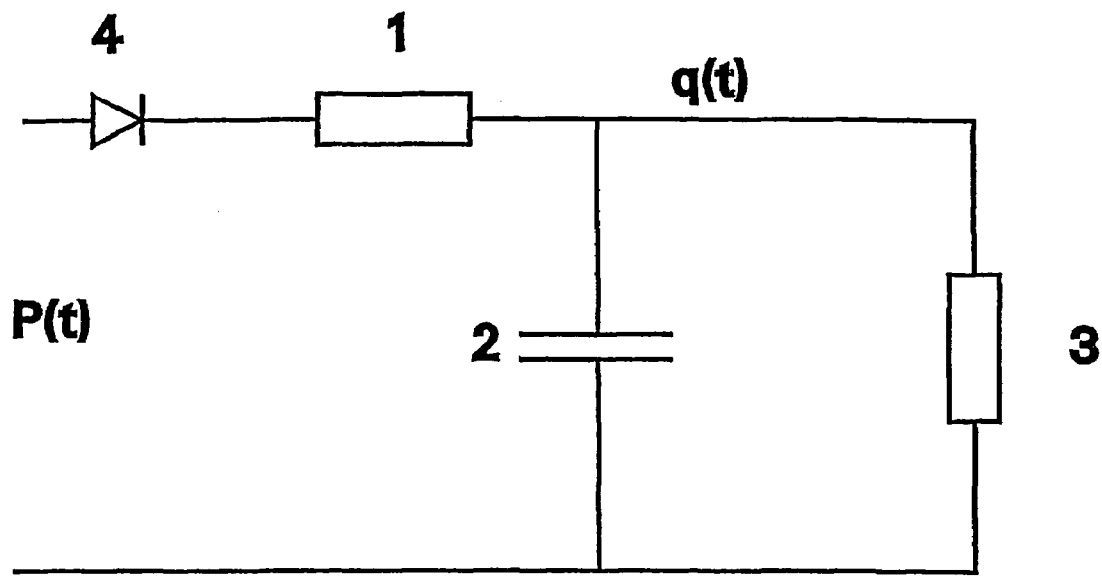
FIG. 1 shows an equivalent circuit diagram of the heart valve and the arterial vascular system, a so-called Windkessel model.
Figure 2:
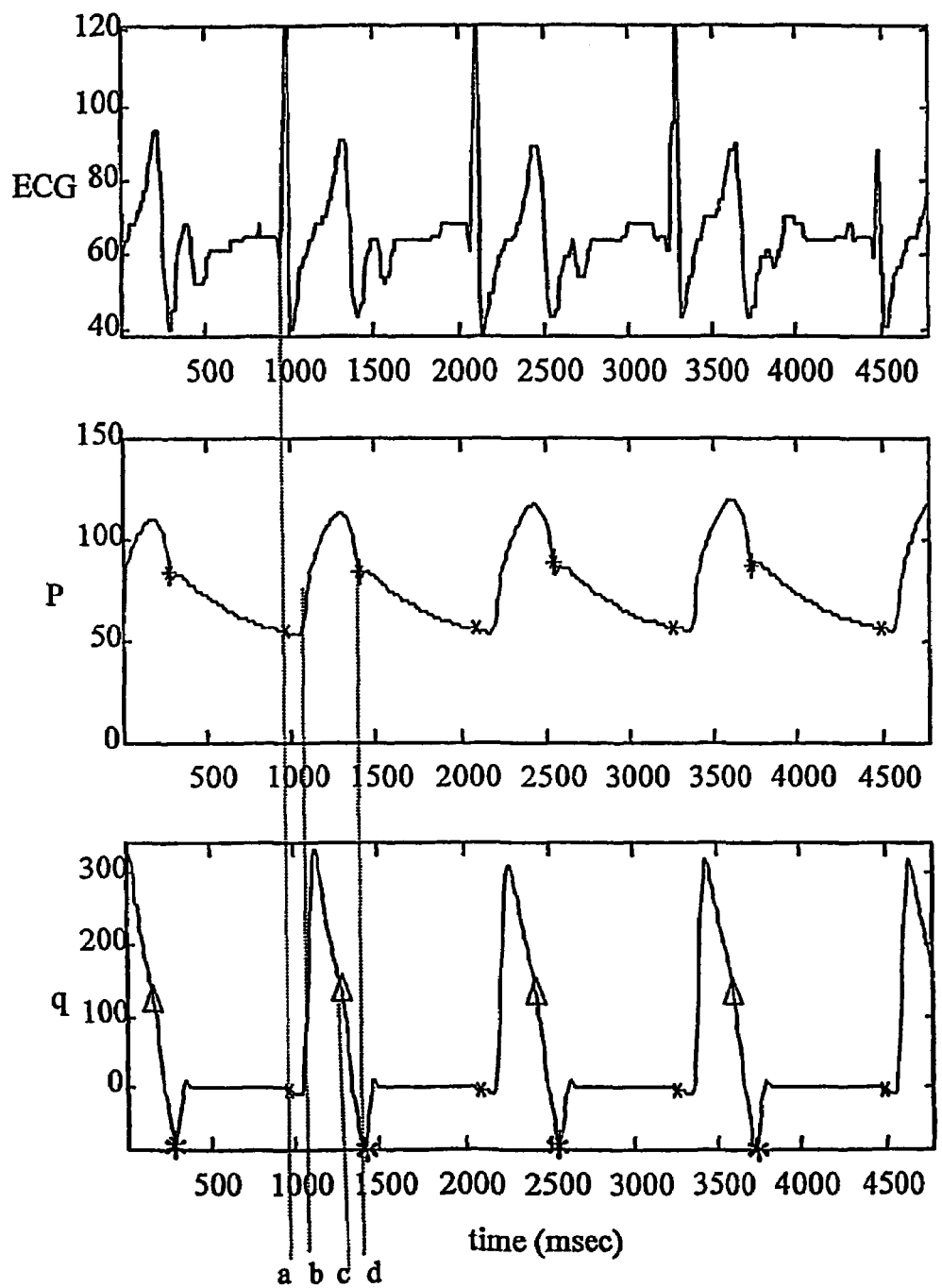
FIG. 2 shows an example of the curve of a measured arterial pressure P(t), the computed blood flow rate q(t), and the electrocardiogram (ECG). Plotted on the vertical axis are P(t), in millimetres of mercury pressure (mmHg), q(t), in arbitrary units (a.u.) and the ECG (a.u.). Plotted on the horizontal axis is the time (time), in milliseconds (msec).
Figure 3:
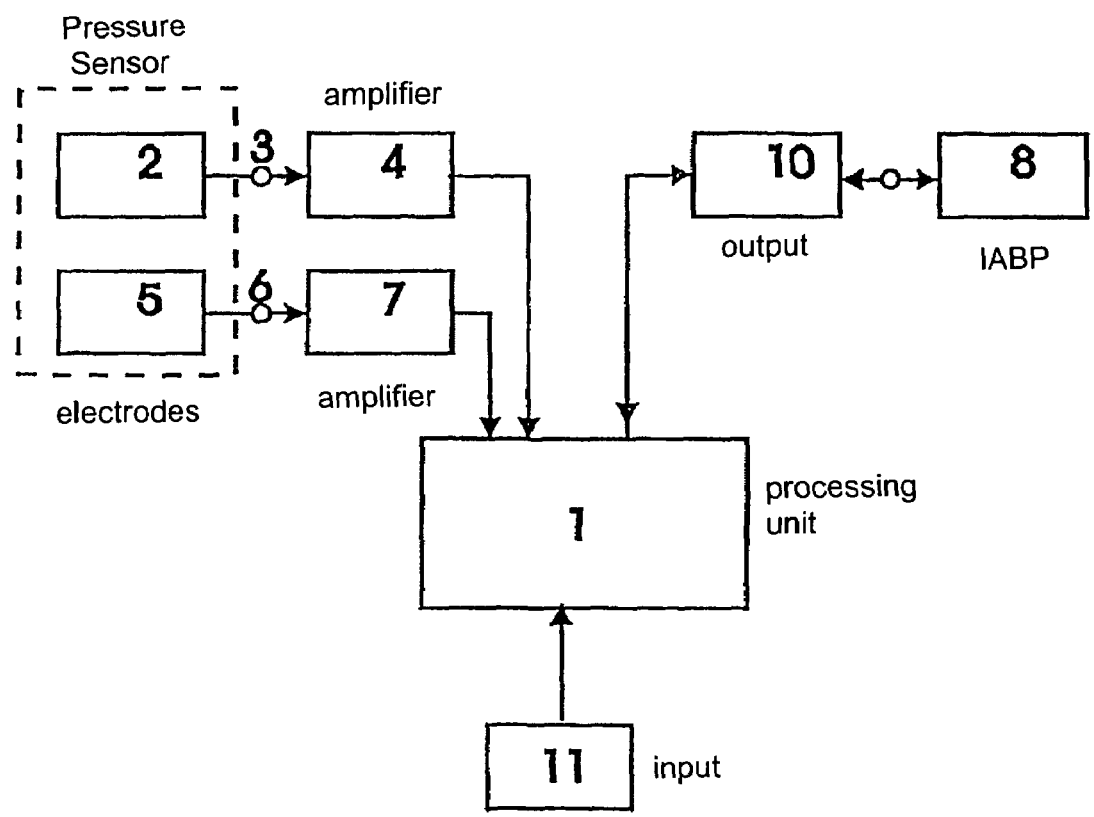
FIG. 3 is a block diagram showing a possible embodiment of the device according to the invention. Reference character: 1—processing unit, 2—blood pressure sensor, 3—input for blood pressure signal from blood pressure sensor, 4—amplifier, 5—electrodes to record electrocardiogram (EGG), 6—input for EGG signal from EGG electrodes, 7—amplifier, 8—intra-aortic balloon pump (IABP), 10—output element, 11—input for inputting patient-related data and mechanical delay time of the IABP.

Before describing the invention in detail, it is useful to describe the principles of the invention first with reference to FIGS. 1, 2, 3.

FIG. 1 shows a Windkessel model which is an equivalent circuit diagram of the heart valve and the arterial vascular system describing the load on the heart. The model comprises the following elements: a characteristic input resistance, Rao, 1; an arterial compliance, Cw, 2; a peripheral resistance, Rp, 3; and a heart valve, D, 4, which closes after the blood flow rate in the cardiac cycle becomes negative. On the basis of this model, a mathematical equation can be written, which gives the relation between the arterial pressure signal, P(t) and the blood flow rate, q(t):

$$(1+Rao/Rp).q(t)+Rao.Cw.q'(t)=P(t)/Rp+Cw.P'(t)$$

wherein q'(t) and P'(t) are the first-order derivatives in time of q(t) and P(t).

The value q(t) that is computed by means of this equation is undelayed in time. The closing time of the heart valve can be accurately derived from the blood flow rate that has thus been computed by determining the time of the first local minimum after the beginning of the ejection phase of the heart. In order to arrive at an accurate computation of q(t), it is important that the correct value for Rp be known. The value of Rp can be computed from Rao and Cw by assuming that the total amount of blood that flows into the arterial vascular system during a heartbeat, or over a number of heartbeats, will also flow out of said arterial vascular system again. In other words, q(t)=0 is the value of q(t) to arrive at at the end of a heartbeat. Although a fixed value for Rao and Cw already leads to good results for the computation of q(t), a further improvement as regards the estimation of Rao and Cw can be obtained by using a table wherein the age and the sex of the person in question are used as parameters.

FIG. 2 shows that the R wave in the ECG (time a) announces the opening of the aortic valve (time b) ahead in time, and that the incisura or the dip in the blood pressure or the negative dip in the computed blood flow rate indicates the closing time of the aortic valve (time c). As a result of the mechanical properties of the IABP, the initiation of the inflation and deflation of the IAB must take place before the closing time and the opening time, respectively, of the aortic valve. Detection of the R wave in the ECG allows a reasonably accurate initiation of the deflation time of the balloon. However, the detection of the negative dip in the computed blood flow rate (time c) coincides with the opening time of the heart valve.

In practice it has become apparent that the time required for inflation the balloon is about 40 msec, for example. The computed blood flow rate makes it possible, however, to predict the closing time of the heart valve by said 40 msec ahead in time. Accordingly, a signal instructing the IABP to inflate the balloon can be delivered to the IABP at a point in time 40 msec before the closing of the heart valve.

To this end the maximum blood flow rate is determined first from the curve of the computed blood flow rate. The maximum in the blood flow rate q(t) can be determined by means of a well-known computing method. Thus it is possible to compare respectively three successive values in the curve of q(t), with a time interval dt, with each other. If the condition q(t−dt)<q(t)>q(t+dt) is met, the maximum is reached at time t. Then a threshold value is selected, for example 40% of the maximum value that has just been found. The selected threshold value depends on the inertia of the IABP (a slow responding IABP gives a higher threshold value). If the conditions q(t−dt) is greater than the threshold value and q(t) is equal to or larger than the threshold value are met after reaching the maximum in the blood flow rate, a signal will be delivered to the IABP to inflate the balloon. By selecting a sufficiently small value for dt, the passing of the threshold value can be signalled practically the time this happens. Preferably, dt is less than 0,005 sec (5 msec).

FIG. 3 is a strongly simplified block diagram of a possible embodiment of the invention. The device that is shown therein comprises a processing unit 1, which includes an output element 10, by means of which an intra-aortic balloon pump 8 can be controlled. The processing unit has three inputs. Input 3 receives a blood pressure signal from a pressure sensor 2. The pressure signal is passed to the processing unit 1 via an amplifier 4. Input 6 receives an electrocardiogram signal from electrodes 5 and this ECG signal is passed to processing unit 1 via amplifier 7. Further, an input 11 is provided for inputting patient-related data, such as the patient's age and sex, and for the mechanical delay time of the IABP 8.

The processing of information by the processing unit takes place in four steps:

In step 1, the patient's age and sex and the predetermined mechanical delay time of the IABP are input via the input 11.

In step 2, the beginning of the pre-ejection phase is to be detected, for example from the R wave of the ECG (time a marked with x in FIG. 2), and a signal instructing the IABP 8 to deflate the balloon is delivered via output element 10. As long as the beginning of the pre-ejection phase has not been detected yet, the blood flow rate is put at q(t)=0. Once the beginning of the ejection phase has been detected, the process proceeds to step 3.

In step 3, the curve of the blood flow rate q(t) is computed from the blood pressure signal P(t), for example by means of the equation:

$$(1+Rao/Rp).q+Rao.Cw.q'=P/RP+Cw.P'$$

When the first maximum in the computed blood flow rate is reached, a threshold value which is a percentage of the maximum value that has just been found is computed. The moment that q(t) is smaller than or equal to the threshold value (time c marked with ^ in FIG. 2), a signal instructing the IABP 8 to inflate the balloon is delivered and the process proceeds to step 4.

Step 4. As soon as q(t)<0, the search for the first local minimum in q(t) is started (time d marked with * in FIG. 2). Once the first minimum has been reached, step 2 restarts for the next heartbeat.

Monitoring of the pressure in the aorta makes it possible to visually detect whether the time of inflation of the balloon has been selected correctly. The inflation of the balloon will be accompanied by an increase of the blood pressure. The time at which the blood pressure increases must coincide with the time at which the heart valve closes, which time can be recognized from the negative dip in the computed blood flow rate q(t). In order to correct a setting which is not optimal, so as to compensate for the delay in the IABP, adjustment of the threshold value can take place via the input element 11 in the course of the above-described sequence of steps.

The invention is not restricted to the above described embodiments which can be varied in a number of ways within the scope of the claims.

The invention claimed is:

1. An apparatus for controlling a heart assist device, comprising a processing unit for computing the blood flow rate (q(t)) from the arterial pressure curve and for predicting at every heartbeat the closing time of the heart valve from the curve of the blood flow rate, wherein the processing unit is adapted to deliver a signal for controlling a heart assist device at a point in time, a period ahead in time of the closing time of the heart valve, wherein the mechanical properties of said heart assist device are taken into account in determining said period, wherein the processing unit is adapted to determine said period by determining the maximum of the blood flow rate curve, taking a percentage of said maximum as a threshold value, and comparing the computed blood flow rate with said threshold value to determine said point in time, and wherein said threshold value is greater than q(t)=0.

2. The apparatus according to claim 1, wherein said heart assist device is an intra-aortic balloon pump having a balloon, wherein said signal initiates the inflation of the balloon.

3. The apparatus according to claim 1, characterized in that the processing unit is arranged for automatically controlling an intra-aortic balloon pump, wherein the deflation of the balloon is initiated on the basis of a derivative from the electrocardiogram with every heartbeat.

4. The apparatus according to claim 1, wherein computation of the curve of the blood flow rate from the arterial blood pressure is based on a Windkessel model that comprises a characteristic input resistance, an arterial compliance, and a peripheral resistance.

5. A method for controlling a heart assist device, comprising computing the blood flow rate (q(t)) from the arterial pressure curve and predicting at every heartbeat the closing time of the heart valve from the curve of the blood flow rate, wherein a signal for controlling a heart assist device is delivered at a point in time, a period ahead in time of the closing time of the heart valve, wherein the mechanical properties of said heart assist device are taken into account in determining said period, wherein said period is determined by determining the maximum of the blood flow rate curve, taking a percentage of said maximum as a threshold value, and comparing the computed blood flow rate with said threshold value to determine said point in time, and wherein said threshold value is greater than q(t)=0.

6. The method according to claim 5, wherein an intra-aortic balloon pump is controlled automatically, wherein the deflation of the balloon is initiated on the basis of a derivative from the electrocardiogram with every heartbeat.

7. The method according to claim 5, wherein computation of the curve of the blood flow rate from the arterial blood pressure is based on a Windkessel model that comprises a characteristic input resistance, an arterial compliance, and a peripheral resistance.

8. The method according to claim 5, wherein said heart assist device is an intra-aortic balloon pump having a balloon, wherein said signal initiates the inflation of the balloon.

9. An apparatus for controlling a heart assist device, comprising a processing unit for computing the blood flow rate from the arterial pressure curve and for predicting at every heartbeat the closing time of the heart valve from the curve of the blood flow rate, wherein the processing unit is adapted to deliver a signal for controlling a heart assist device at a point in time, a period ahead in time of the closing time of the heart valve, wherein the mechanical properties of said heart assist device are taken into account in determining said period, wherein the processing unit is adapted to determine said period by determining the maximum of the blood flow rate curve, taking a percentage of said maximum as a threshold value, and comparing the computed blood flow rate with said threshold value to determine said point in time, wherein said heart assist device is an intra-aortic balloon pump having a balloon, wherein said signal initiates the inflation of the balloon, and wherein said signal to inflate said intra-aortic balloon pump is delivered about 40 msec ahead of the closing time of the heart valve.

10. The apparatus according to claim 9, characterized in that the processing unit is arranged for automatically controlling the intra-aortic balloon pump, wherein the deflation of the balloon is initiated on the basis of a derivative from the electrocardiogram with every heartbeat.

11. The apparatus according to claim 9, wherein computation of the curve of the blood flow rate from the arterial blood pressure is based on a Windkessel model that comprises a characteristic input resistance, an arterial compliance, and a peripheral resistance.

12. A method for controlling a heart assist device, comprising computing the blood flow rate from the arterial pressure curve and predicting at every heartbeat the closing time of the heart valve from the curve of the blood flow rate, wherein a signal for controlling a heart assist device is delivered at a point in time, a period ahead in time of the closing time of the heart valve, wherein the mechanical properties of said heart assist device are taken into account in determining said period, wherein said period is determined by determining the maximum of the blood flow rate curve, taking a percentage of said maximum as a threshold value, and comparing the computed blood flow rate with said threshold value to determine said point in time, wherein said heart assist device is an intra-aortic balloon pump having a balloon, wherein said signal initiates the inflation of the balloon, and wherein said signal to inflate said intra-aortic balloon pump is delivered about 40 msec ahead of the closing time of the heart valve.

13. The method according to claim 12, wherein the intra-aortic balloon pump is controlled automatically, wherein the deflation of the balloon is initiated on the basis of a derivative from the electrocardiogram with every heartbeat.

14. The method according to claim 12, wherein computation of the curve of the blood flow rate from the arterial blood pressure is based on a Windkessel model that comprises a characteristic input resistance, an arterial compliance, and a peripheral resistance.

* * * * *